(12) United States Patent
Deboeuf et al.

(10) Patent No.: US 10,653,490 B2
(45) Date of Patent: May 19, 2020

(54) CHAIN FOR TRANSMITTING MOVEMENT BETWEEN ACTUATORS AND THE BASE OF A MEMBER FOR DRIVING A MOVABLE ELEMENT

(71) Applicant: ROBOCATH, Rouen (FR)

(72) Inventors: Sebastien Deboeuf, Sotteville-les-Rouen (FR); Fabien Destrebecq, Bourgtheroulde (FR); Bruno Fournier, Saint Ouen (FR); Philippe Bencteux, St Martin du Vivier (FR)

(73) Assignee: ROBOCATH, Rouen (FR)

( * ) Notice: Subject to any disclaimer, the term of this patent is extended or adjusted under 35 U.S.C. 154(b) by 380 days.

(21) Appl. No.: 15/580,703

(22) PCT Filed: Jun. 10, 2016

(86) PCT No.: PCT/FR2016/051400
§ 371 (c)(1),
(2) Date: Dec. 8, 2017

(87) PCT Pub. No.: WO2016/198800
PCT Pub. Date: Dec. 15, 2016

(65) Prior Publication Data
US 2018/0185108 A1    Jul. 5, 2018

(30) Foreign Application Priority Data
Jun. 12, 2015  (FR) ...................................... 15 55377

(51) Int. Cl.
*A61B 34/35*    (2016.01)
*A61B 34/30*    (2016.01)

(52) U.S. Cl.
CPC .............. *A61B 34/35* (2016.02); *A61B 34/30* (2016.02); *A61B 2034/301* (2016.02)

(58) Field of Classification Search
CPC ......... A61B 34/30; A61B 34/32; A61B 34/35; A61B 34/37; A61B 34/70; A61B 34/71;
(Continued)

(56) References Cited

U.S. PATENT DOCUMENTS

| 5,389,849 A | * | 2/1995 | Asano ........................ B25J 3/04 |
| | | | 310/323.21 |
| 10,028,796 B1 | * | 7/2018 | Abe ........................ A61B 34/74 |

(Continued)

FOREIGN PATENT DOCUMENTS

| WO | 2008/115151 A1 | 9/2008 |
| WO | 2014/135813 A1 | 9/2014 |

OTHER PUBLICATIONS

International Search Report, dated Sep. 5, 2016, from corresponding PCT/FR2016/051400 application.

*Primary Examiner* — Dianne Dornbusch
(74) *Attorney, Agent, or Firm* — Young & Thompson

(57) ABSTRACT

Disclosed is a movement transmission chain including: a base of a driving member for driving a movable element; and three actuators controlling the base of the driving member in three movement directions orthogonal to one another, by element of three interfaces with the base of the driving member, the mid-surfaces of the three interfaces intersecting in a central region of the base of the driving member.

15 Claims, 4 Drawing Sheets

(58) Field of Classification Search
CPC ......... A61B 34/72; A61B 34/73; A61B 34/74; A61B 34/75; A61B 34/76; A61B 34/77; A61B 2034/301; A61B 2034/302; A61B 2034/303; A61B 2034/305; A61B 1/77; A61B 1/0016; A61M 25/01

See application file for complete search history.

(56) References Cited

U.S. PATENT DOCUMENTS

| | | | | |
|---|---|---|---|---|
| 2002/0156365 A1* | 10/2002 | Tsekos | ............... | A61B 5/0555 600/411 |
| 2009/0082722 A1* | 3/2009 | Munger | ............. | A61M 25/0113 604/95.01 |
| 2009/0171151 A1* | 7/2009 | Choset | ................ | A61B 34/20 600/114 |
| 2009/0261690 A1* | 10/2009 | Mashimo | ............ | A61B 8/4488 310/323.03 |
| 2010/0170361 A1* | 7/2010 | Bennett | ................ | A61B 34/71 74/490.04 |
| 2011/0278417 A1* | 11/2011 | Diamond | ............ | A63H 33/003 248/349.1 |
| 2012/0298719 A1* | 11/2012 | Shelton, IV | ..... | A61B 17/07207 227/176.1 |
| 2014/0058406 A1* | 2/2014 | Tsekos | ................ | A61B 34/30 606/130 |
| 2014/0228861 A1* | 8/2014 | Kishi | ................... | A61B 34/37 606/130 |
| 2014/0246471 A1* | 9/2014 | Jaworek | ............ | A61B 17/068 227/175.1 |
| 2014/0277333 A1* | 9/2014 | Lewis | ............... | A61M 25/0113 623/1.11 |
| 2014/0277334 A1* | 9/2014 | Yu | ......................... | A61B 34/30 623/1.11 |
| 2014/0305987 A1* | 10/2014 | Parihar | ............... | A61B 17/115 227/175.2 |
| 2015/0173819 A1* | 6/2015 | Tang | .................... | A61B 17/60 606/86 R |
| 2015/0297864 A1* | 10/2015 | Kokish | ............. | A61M 25/0113 604/95.04 |
| 2016/0008076 A1* | 1/2016 | Bencteux | .......... | A61M 25/0113 604/95.04 |
| 2016/0038239 A1* | 2/2016 | Yamanaka | ............ | A61B 34/30 606/130 |
| 2016/0135830 A1* | 5/2016 | Volkmer | ............... | A61B 17/29 606/206 |
| 2018/0079074 A1* | 3/2018 | Devengenzo | .......... | G01L 5/226 |
| 2018/0080841 A1* | 3/2018 | Cordoba | ............. | B25J 15/0019 |
| 2018/0085178 A1* | 3/2018 | Komuro | ................ | A61B 34/35 |
| 2018/0116741 A1* | 5/2018 | Garcia Kilroy | ....... | G01L 3/1428 |
| 2018/0214219 A1* | 8/2018 | Overmyer | ............ | B25J 9/1692 |
| 2018/0243035 A1* | 8/2018 | Kopp | ..................... | A61B 34/37 |
| 2018/0310948 A1* | 11/2018 | Stamm | ............... | A61B 18/1445 |
| 2019/0239966 A1* | 8/2019 | Xu | ......................... | A61B 34/70 |
| 2019/0269473 A1* | 9/2019 | Takayama | ............... | B25J 18/06 |

\* cited by examiner

CHAIN FOR TRANSMITTING MOVEMENT BETWEEN ACTUATORS AND THE BASE OF A MEMBER FOR DRIVING A MOVABLE ELEMENT

The present invention relates to the chains for transmission of movement between several actuators and a drive member for a mobile element. The mobile element can in particular be a catheter or a catheter guide, but not necessarily.

The manual insertion of a catheter or a guide in a patient is a relatively conventional surgical procedure. However, since this procedure is monitored by x-rays, the surgeon in charge of this procedure is subject to significant irradiation if the surgeon does such an operation on many patients.

In order to reduce the risks for the surgeon, it is attempted to make such an insertion robotic. Making it robotic is complex because it is difficult to grasp the catheter. The catheter is in fact bathed in storage liquid and must remain sterile. Further, it is desirable to be able to command movements of translation and alternating and/or simultaneous rotation of the catheter. The reliability of these robotic systems is a decisive criterion.

In robotic modules from the prior art, whether in the medical field of catheters or in other fields, the actuators, which transmit the movement thereof to the drive member, transmit it by means of respective interfaces between the respective actuators and the base of the drive member.

Hence, in these robotic modules in the prior art, the interfaces are located outside of the base of the drive member or in the peripheral region of the base of the drive member.

The implementation structure of these interfaces between actuators and drive member base is then relatively simple.

The invention has however detected a problem of reliability for the transmission of the movement between actuators and drive member base in that case.

In fact, the invention has shown that this reliability problem comes from the off-center nature of the position of the interfaces, then driving in imbalanced transmission of the force.

Further, each actuator only supports the force in the direction thereof, there is nothing to carry one or more other actuators in one or more other directions, as could be the case in existing systems: the bulk and weight are sharply reduced that way.

This is why, the invention proposes to arrange the interfaces such that the intersection thereof is located in a central region of the base of the drive member, even preferably at the center of gravity of the base of the drive member, then allowing a balanced transmission of the force, driving a reliable transmission of movement between actuators on the one side and drive member base on the other.

This involves placing the interfaces inside the base of the drive member, which makes the structure relatively more complex, but distinctly more reliable as it involves the quality of transmission of movement between actuators on the one side and drive member base on the other.

The base of the drive member is secured to the drive member and fixed relative to the drive member.

For this purpose, according to the invention, a movement transmission chain is provided comprising:
 A drive member base for a mobile element;
 Three actuators piloting the base of the drive member respectively along three mutually distinct translation directions, by means of three respective interfaces with the base of the drive member;
 Characterized in that the intersection of the average surfaces of the three interfaces is located in the central region of the base of the drive member.

For this purpose, according to the invention, a movement transmission chain is also provided comprising:
 A base of the drive member for a mobile element;
 Three actuators piloting the base of the drive member respectively along three mutually distinct translation directions, by means of three respective interfaces with the base of the drive member;
 Characterized in that the three interfaces are substantially flat;
 In that the three interfaces are mutually orthogonal;
 And in that these three interfaces are nested in each other.

In preferred embodiments of the invention, use could further be made of one and/or the other of the following arrangements:

Preferably the three translation directions are mutually orthogonal.

Preferably, the three interfaces are substantially flat, these three interfaces are mutually orthogonal, and these three interfaces are nested inside each other. In that way, the three interfaces can be concentrated relatively simply and truly effectively in the central region of the base of the drive member.

Preferably, the three interfaces are pressure plates transmitting the respective thrusts from the three actuators. With these flat plates, an effective transmission of thrust from the actuators is possible for relatively reduced overall volume.

Preferably, the first plate comprises two mutually orthogonal openings which are respectively traversed by a second plate and a third plate, the second plate comprises an opening which is traversed by the third plate, where the opening of the second plate is orthogonal to the two openings of the first plate, and the third plate is not traversed either by the first plate or the second plate. This way of nesting the plates inside each other is structurally relatively simple and still effective.

Preferably, each of these openings allows a travel of the plate passing through it, with this travel corresponding to the range of the actuator of the plate which passes through said opening, where this travel is greater than the thickness of the plate which passes through said opening. In fact, if one of the actuators moves, the base of the drive member must only move in the direction corresponding to this actuator which moved and not in the two directions corresponding to the actuators remaining motionless. To do that, the presence of these travels serves to disconnect the transmission of force coming from each of the various actuators from each other.

Preferably, each plate is mobile in translation along a direction parallel to the straight-line formed by the intersection of the two other plates. In that way the transmission of pairwise orthogonal forces between the actuators is easily maintained.

Preferably, each plate is connected to its actuator by two struts symmetric about the thrust axis of said actuator, preferably by four struts symmetric about the thrust axis of said actuator. Thus, the transmission of force from the actuator is well distributed on the corresponding plate.

Preferably, the base of the drive member is fixedly secured with each of the interfaces in a way that the movement of one of the interfaces automatically leads to the same movement of the base of the drive member. Thus, the transmission of force between the interfaces on the one side and the drive member base on the other is more direct.

Preferably, the base of the drive member is a cube inside of which the three interfaces are located. Thus, the overall volume of the base of the drive member is relatively reduced, whereas the interfaces are just the same fully contained inside the base of the drive member. The overall compactness thereof is consequently improved.

Preferably, the base of the drive member is a cube resulting from the assembly of eight smaller cubes assembled around interfaces. These eight small cubes represent the minimum number of subparts of the cube making up the base of the drive member so as to be able to assemble this cube around the set of three interfaces nested in each other.

Preferably, each plate is lodged between four smaller cubes on one side and four smaller cubes on the other side. The drive member base is thus completely symmetric and balanced.

Preferably, the central region is the center of gravity of the base of the drive member. The transmission of forces between actuators and drive member base is thus perfectly balanced because of the perfectly centered nature of the interfaces relative to the base of the drive member.

Preferably, the movement transmission chain includes a mobile element driven by the drive member.

Preferably, the materials used are low or even very low friction materials in order to allow interfaces nested in each other to slide easily.

In a preferred but nonexclusive application, the mobile element is a catheter or catheter guide, the drive member is a tightening member for a catheter or a catheter guide.

Other features and advantages of the invention will become apparent during the following description of one of the embodiments thereof, given as a nonlimiting example, with reference to the attached drawings.

In the various figures, the same references designate identical or similar items.

Figure 1:
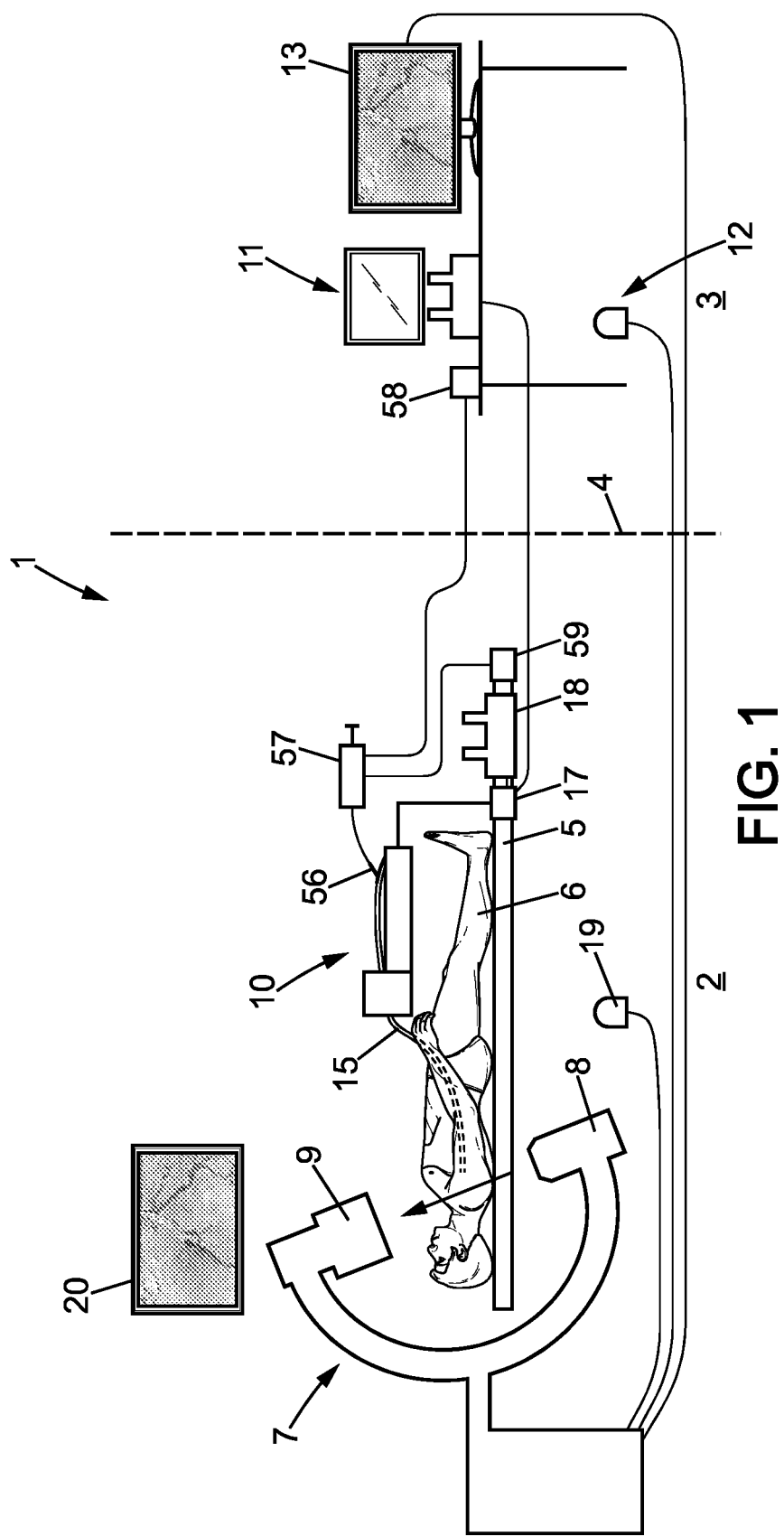
FIG. 1 is a schematic side view of a robotic arteriographic installation.

FIG. 1 schematically shows an arteriographic installation 1. The arteriographic installation 1 is divided into two distinct areas: one operating room 2 and one command room 3. The command room 3 can be close to the operating room 2, separated from it by a simple x-ray blocking wall 4, or remote. The equipment in the operating room 2 and the command room 3 are functionally connected to each other by wire, wireless or network, etc.

The operating room 2 includes an operating table 5 receiving a patient 6. The operating room 2 can also include a medical imager 7 in particular for imaging by x-ray, comprising a source 8 and a detector 9 arranged on either side of the patient, which could be mobile relative to the patient.

The arteriographic installation 1 comprises a robot 10 arranged in the operating room 2.

The arteriographic installation 1 comprises a command station 11 arranged in the command room 3. The command station 11 is suited for remotely commanding the robot 10. The arteriographic installation 1 can also include, arranged in the control room 3, one or more remote controls 12 for the imager 7 communicating with the imager 7 for controlling it from a distance. The arteriographic installation 1 can also include, arranged in the command room 3, a screen 13, communicating with the imager 7, for viewing in real time in the command room 3 the images acquired by the imager 7.

The robot 10 can include a container suited for holding a long flexible medical member 15 to be inserted in a patient's body. The long flexible medical member 15 could for example involve a member to be inserted in a canal of a patient and to be moved in this canal, in particular an artery or vein of the patient, through a catheter introducer providing an access opening into the patient. The long flexible medical member can in particular be a catheter. As a variant, the long flexible medical member can be a catheter guide. A guide generally has a transverse diameter less than that of the catheter, which is generally hollow over a portion close to the patient, even over its entire length, such that the guide can be displaced inside of it, in particular inside the body of the patient. The guide can also comprise a bent-back end.

The robot 10 may include a drive module for the long flexible medical member 15. The drive module can be commanded from the command station 11 for driving the long flexible medical member relative to the patient along at least one degree of freedom, as will be described in detail subsequently. The drive module may include a communication box 17 providing an interface with the command station 11. As needed, the robot 10 may include a local command box 18, intended to command the robot from the operating room 2 if necessary.

It will additionally be noted that all commands and feedback available in the command room 3 can also be available in the operating room 2 in order for local operation, such as for example a command 19 for the imager and the screen 20 with which to see the images acquired by the imager 7.

The hollow long flexible medical member 15 can be connected to a connector 56 with which to inject a contrast product making the imaging inside the long flexible medical member easier. The arteriographic installation can include a contrast product injector 57 connected to the connector 56 and commanded by a command 58 arranged in the command room 3. A command 59 for the contrast product injector can also be present locally in the operating room 2.

Figure 2:
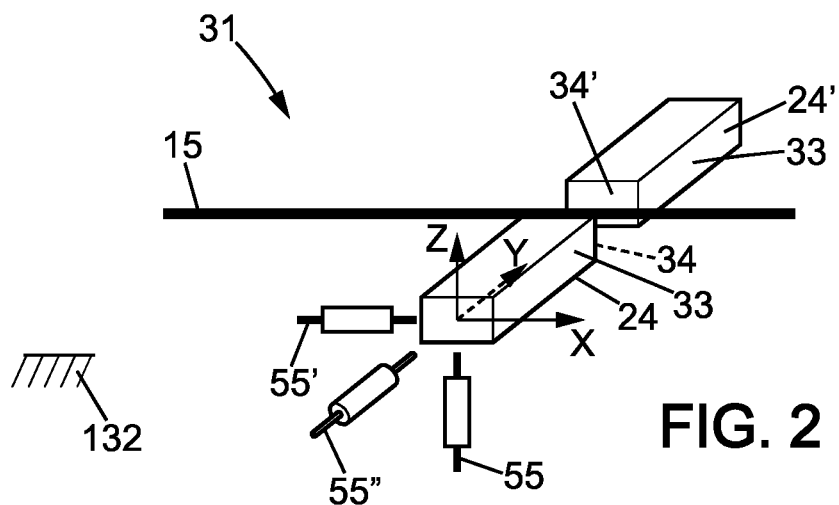
FIG. 2 is a perspective sketch of a portion of a drive module in released configuration.

FIG. 2 shows a drive module 31 according to a first embodiment. This drive module 31 is suited for driving a long flexible medical member 15 extending along the longitudinal direction X. It will be noted that the longitudinal direction X near the drive module 31 is not strictly the same as that of the long flexible medical member 15 near its end but that a translation and/or a rotation of the long flexible medical member 15 along/around the longitudinal direction X near the drive module 31 will drive a translation and/or a rotation of the long flexible medical member 15 respectively along/around the longitudinal direction thereof near the end thereof.

The drive module 31 includes a base 132 and at least one drive member 24 mounted mobile relative to the base 132. The drive member 24 is, for example, mounted mobile relative to the base 132.

In the example shown, the drive module 31 further comprises a second drive member 24'. The drive member 24, also called hereafter first drive member, and the second drive member 24' together form a pair of drive members 33. The pair of drive members 33 comprises two drive members which together engage for generating a movement of the long flexible medical member 15 relative to the base 132. In the example shown, the second drive member 24' is mounted mobile relative to the base 132. The second drive member 24' is, for example, mounted mobile relative to the base 132.

The first drive member 24 and the second drive member 24' are paired for simultaneous movement. For example, the first and second drive members 24, 24' can be commanded individually, independently of each other, but according to synchronized respective commands. As a variant, a shared command can be provided which is distributed to one and the other of the first and second drive members 24, 24' by mechanical or electronic connection between their command systems.

Each drive member 24, 24' comprises a drive surface 34, 34' respectively. The long flexible medical member 15 is arranged between the drive surfaces 34, 34' of the drive members 24, 24' of a single pair. To set the ideas, the drive surfaces 34, 34' are separated from each other along the direction Y.

The pair of drive members 24, 24' can be placed in a released configuration, shown in FIG. 2, in which the drive surface 34, 34' of the drive members 24, 24' of the pair of drive members 33 is not engaged with the long flexible medical member 15.

The pair of drive members 33 can be placed in a drive configuration in which the drive surfaces 34, 34' of the drive members of the pair of drive members are engaged with the long flexible medical member 15 to be driven. The force applied by a drive member on the long flexible medical member in this configuration is for example of order a few Newtons (5-30 N for example). The restoring means, described above, are arranged for example to return the pair of drive members to released configuration, which provides a safety function, for example in case of outage of electric power.

To place the pair of drive members 33 alternately in released and drive configurations, a relative displacement of one towards the other of the two drive members 24, 24' can be ordered. This displacement can for example be the displacement of one drive member 24 relative to the base with the other remaining fixed. As a variant, the two drive members 24, 24' can both move towards each other relative to the base.

In the example, a displacement along the Y direction is intended.

In the embodiment shown, both drive members 24, 24' are mobile relative to the base along one degree of freedom. This degree of freedom is different from the one allowing the alternate placement of the drive members in the released and drive positions. It is in particular provided that the drive members 24, 24' are mobile relative to the base along one degree of freedom in their drive configuration. Thus, the displacement of the drive members along one degree of freedom in their drive configuration generates a displacement of the long flexible medical organ relative to the base 132.

An example of reduction of such a system to practice is shown below in connection with FIG. 3.

This sample embodiment is provided solely for illustration of a concrete sample embodiment of an actuation system.

Figure 3:
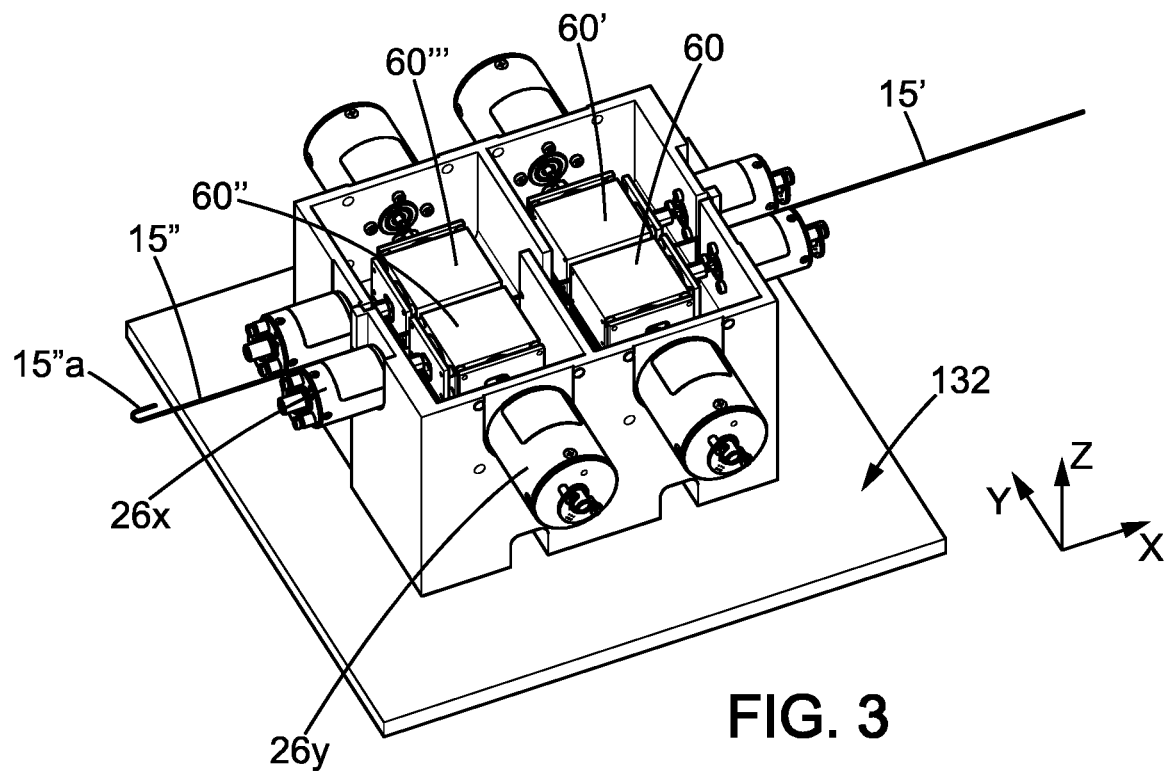
FIG. 3 is a perspective view of a sample embodiment of the actuation system.

FIG. 3 includes a fixed base 132 shared by four actuation systems. Each actuation system commands the movement of one respective drive member, not shown, secured to a respective cube 60, 60', 60", 60'''. The cubes 60, 60', 60", 60''' correspond respectively to drive members not shown in the figure. These cubes 60, 60', 60", 60''' are the corresponding drive member bases.

The reference 15 is used for designating alternatively the guide 15", the catheter 15', or generally a long flexible medical member to be inserted into the body of the patient. It can for example involve a catheter for a procedure. Such a catheter for a procedure can have a diameter less than the catheter, so as to be guided inside thereof, coaxially inside the patient, and be hollow so as to be guided on the guide inside the patient.

The guide 15" has a front end 15''' a slightly curved relative to the main longitudinal axis of the guide and extending out from the front end of the catheter 15'. The catheter 15' can undergo two distinct motions:

A translation along the longitudinal axis thereof;

A rotation around the longitudinal axis thereof.

These movements can be generated in one direction or the other.

As needed, the catheter 15' can undergo a combined movement of the two simple movements described above.

As needed, the catheter 15' can undergo two combined movements of the two simple movements described above, according to combinations.

What was described above concerning the catheter also applies to the guide.

In some cases, the catheter itself is provided with a curved end, either in order to allow navigation on the same principle as a guide, or to facilitate positioning in an anatomical area having a specific curvature.

Subsequently, only the operation of one cube will be described. Reference, as an example, is made to cube 60". The cube 60" is associated with three actuators $26x$, $26y$, $26z$ (this last one is not visible, similar in all ways to the actuators $26x$ and $26y$, and located under the base 132). The actuator $26y$ is used to move the cube 60" along the Y direction, while also allowing a movement of the cube 60" both along the X and Z directions relative to the actuator $26y$ for some range of movement.

Figure 4:
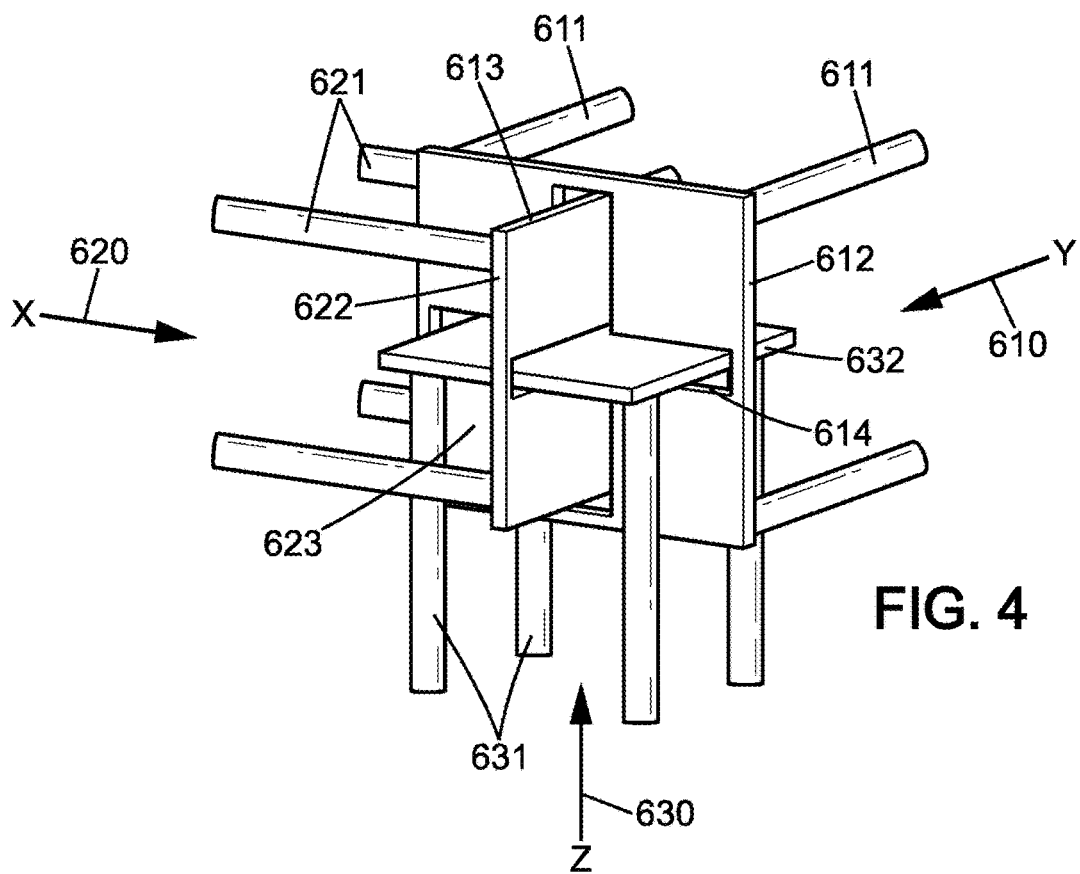
FIG. 4 is a perspective view of a sample embodiment of the intersection and nesting of interfaces between actuators on the one side and drive member base on the other.

FIG. 4 is a perspective view of a sample embodiment of the intersection and nesting of interfaces between actuators on the one side and drive member base on the other.

Three actuators 610, 620, 630 exert a force along three mutually orthogonal directions Y, X, Z.

The actuator 610 exerts the force thereof in the Y direction via four struts 611 pushing the four corners of a first pressure plate 612 which constitutes the interface between the actuator 610 and the base of the drive member. The first plate 612 includes a first opening 613 through which passes a second plate 622 constituting the interface between the actuator 620 and the drive member base. This first opening 613 comprises a travel in the X direction so as to allow the range of the actuator 620 and the associated second plate 622 along the X direction without moving the first plate 612. The first plate 612 includes a second opening 614 through which passes a third plate 632 constituting the interface between the actuator 630 and the drive member base. This second opening 614 comprises a travel in the Z direction so as to allow the range of the actuator 630 and the associated third plate 632 along the Z direction without moving the first plate 612.

The actuator 620 exerts the force thereof in the X direction via four struts 621 pushing the four corners of the second pressure plate 622 which constitutes the interface between the actuator 620 and the base of the drive member. The second plate 622 includes a third opening 623 through which passes a third plate 632 constituting the interface between the actuator 630 and the drive member base. This third opening 623 comprises a travel in the Z direction so as to allow the range of the actuator 630 and the associated third plate 632 along the Z direction without moving the second plate 622.

The actuator 630 exerts the force thereof in the Z direction via four struts 631 pushing the four corners of the second pressure plate 632 which constitutes the interface between the actuator 630 and the base of the drive member. The third plate 632 does not have any opening.

Figure 5:
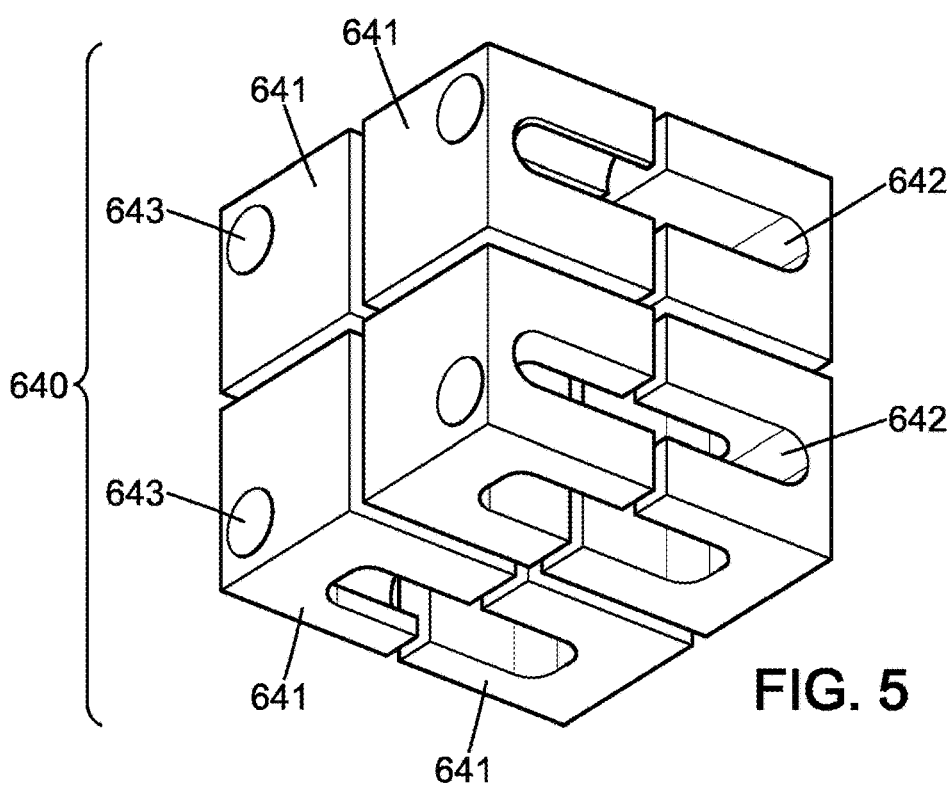
FIG. 5 is a perspective view of a sample embodiment of the drive member base.

FIG. 5 is a perspective view of a sample embodiment of the drive member base.

The base of the drive member includes a cube 640 which could be any one of the cubes 60, 60', 60" or 60"' from FIG. 3. This cube 640 comprises eight small cubes 641 assembled together at the eight vertices of the cube 640. In reality, the small cubes 641 are only portions of small cubes on three faces. Circular opening 643 are arranged on some faces of the small cubes 641 and oblong openings 642 are arranged on other faces of small cubes 641. The circular openings 643, like the oblong opening 642, are intended to receive the struts 611, 621 and 631 from various plates 612, 622 and 632.

Figure 6:
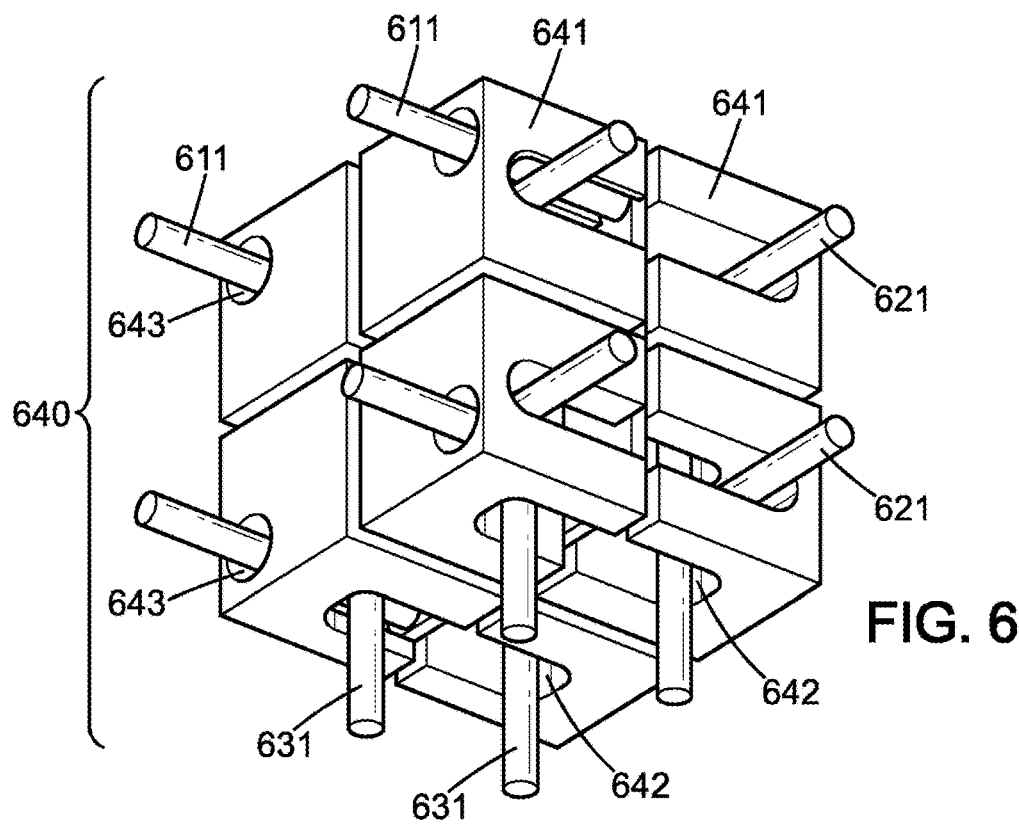
FIG. 6 is a perspective view of a sample embodiment of assembly between the interfaces on the one side and the drive member base on the other.

FIG. 6 is a perspective view of a sample embodiment of assembly between the interfaces on the one side and the drive member base on the other.

The struts 611, 621 and 631 from various plates 612, 622 and 632 can pass more or less deeply in the various openings 642 and 643, in that way allowing plates 612, 622 and 632 respectively to move the cube 640 in the directions Y, X and Z respectively. The plates 612, 622 and 632 push or pull the small cubes 641 forming together the cube 640.

Figure 7:
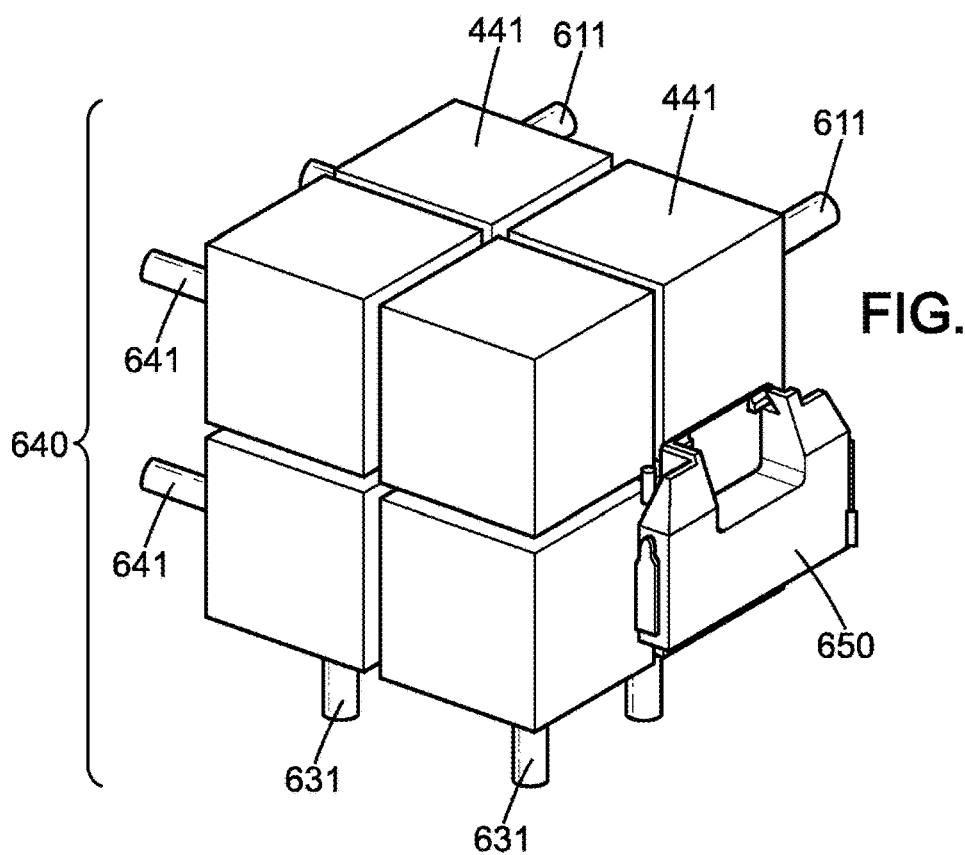
FIG. 7 is another perspective view of a sample embodiment of assembly between the interfaces on the one side and the drive member base on the other.

FIG. 7 is another perspective view of a sample embodiment of assembly between the interfaces on the one side and the drive member base on the other.

On this side, the small cubes 641 do not comprise any opening, but only a key cap 650. This tip 650 is going to be able to securely carry and fix the drive member 24 shown in FIG. 2.

The invention claimed is:

1. A movement transmission chain comprising:
   a drive member base for a mobile element;
   three actuators piloting the base of the drive member respectively along three mutually distinct translation directions, by means of three respective interfaces with the base of the drive member;
   wherein the intersection of the average surfaces of the three interfaces is located in the central region of the base of the drive member;
   wherein the three interfaces are substantially flat;
   these three interfaces are mutually orthogonal;
   and these three interfaces are nested inside each other.

2. The movement transmission chain according to claim 1, wherein: the central region is the center of gravity of the base of the drive member.

3. A movement transmission chain comprising:
   a drive member base for a mobile element;
   three actuators piloting the drive member base respectively along three mutually distinct translation directions, by means of three respective interfaces with the drive member base;
   wherein the three interfaces are substantially flat;
   wherein these three interfaces are mutually orthogonal;
   and wherein these three interfaces are nested inside each other.

4. The movement transmission chain according to claim 3, wherein: the three translation directions are mutually orthogonal.

5. The claim has been amended to remove all reference number, the claim has been replaced with:
   The movement transmission chain according to claim 4, wherein: the three interfaces are pressure plates transmitting the respective thrusts from the three actuators.

6. The movement transmission chain according to claim 5, wherein:
   a first pressure plate of the three interfaces comprises two mutually orthogonal openings which are respectively traversed by a second pressure plate of the three interfaces and a third pressure plate of the three interfaces;
   the second pressure plate comprises an opening which is traversed by the third pressure plate, where the opening of the second pressure plate is orthogonal to the two openings of the first pressure plate; and the third pressure plate is not traversed either by the first pressure plate or the second pressure plate.

7. The movement transmission chain according to claim 6, wherein: each of these openings allows a travel of the pressure plate passing through it, with this travel corresponding to the range of the actuator of the pressure plate which passes through said opening, where this travel is greater than the thickness of the pressure plate which passes through said opening.

8. The movement transmission chain according to claim 5, wherein: each pressure plate is mobile in translation along a direction parallel to the straight-line formed by the intersection of the two other pressure plates.

9. The movement transmission chain according to claim 5, wherein: each pressure plate is connected to its actuator by two struts symmetric about the thrust axis of said actuator, preferably by four struts symmetric about the thrust axis of said actuator.

10. The movement transmission chain according to claim 3, wherein: the base of the drive member is fixedly secured with each of the interfaces in a way that the movement of one of the interfaces automatically leads to the same movement of the base of the drive member.

11. The movement transmission chain according to claim 3, wherein: the base of the drive member is a cube inside of which the three interfaces are located.

12. The movement transmission chain according to claim 11, wherein: the base of the drive member is a cube resulting from the assembly of eight smaller cubes assembled around the three interfaces.

13. The movement transmission chain according to claim 12, wherein: each of the three interfaces is lodged between four smaller cubes on one side and four smaller cubes on the other side.

14. The movement transmission chain according to claim 3, wherein: the movement transmission chain includes a mobile element driven by the drive member.

15. The movement transmission chain according to claim 14, wherein:
   the mobile element is a catheter or a catheter guide;
   the drive member is a tightening member for a catheter or a catheter guide.

* * * * *